United States Patent
Civolani et al.

(10) Patent No.: US 6,349,595 B1
(45) Date of Patent: Feb. 26, 2002

(54) METHOD FOR OPTIMIZING DRILL BIT DESIGN PARAMETERS

(75) Inventors: Lorenzo Civolani, Castel Maggiore; Fabrizio Zausa, Milanese, both of (IT)

(73) Assignee: Smith International, Inc., Houston, TX (US)

( * ) Notice: Subject to any disclaimer, the term of this patent is extended or adjusted under 35 U.S.C. 154(b) by 0 days.

(21) Appl. No.: 09/671,231

(22) Filed: Sep. 27, 2000

Related U.S. Application Data

(60) Provisional application No. 60/157,444, filed on Oct. 4, 1999.

(51) Int. Cl.[7] .............................. E21B 47/00; G01N 3/48
(52) U.S. Cl. ......................................... 73/152.02; 73/81
(58) Field of Search ................................ 73/152.02, 81, 73/85, 152.03, 152.52, 152.59

(56) References Cited

U.S. PATENT DOCUMENTS

| | | | |
|---|---|---|---|
| 5,318,136 A | 6/1994 | Rowsell et al. | 175/24 |
| 5,416,697 A | 5/1995 | Goodman | 364/422 |
| 5,704,436 A | 1/1998 | Smith et al. | 175/27 |
| 5,730,234 A | 3/1998 | Putot | 175/50 |
| 5,794,720 A | 8/1998 | Smith et al. | 185/40 |
| 5,812,068 A | 9/1998 | Wisler et al. | 340/855.5 |
| 6,002,985 A | 12/1999 | Stephenson | 702/13 |
| 6,012,015 A | 1/2000 | Tubel | 702/6 |
| 6,021,377 A | 2/2000 | Dubinsky et al. | 702/9 |
| 6,044,325 A | 3/2000 | Chakravarthy et al. | 702/7 |
| 6,109,368 A | 8/2000 | Goldman et al. | 175/39 |

OTHER PUBLICATIONS

Thiercelin, M. and Cook, J.: "Failure Mechanisms Induced by Indentation of Porous Rocks". Key Questions in Rock Mechanics, pp. 135–142, 1988.

Cook, J.M. and Thiercelin, M.: "Indentation Resistance of Shale: the Effects of Stress State and Strain Rate". Rock Mechanics as a Guide for Efficient Utilization of Natural Resources, pp. 757–764, 1989.

Thiercelin, M.: "Parameters Controlling Rock Indentation"–Rock at Great Depth, Proc. ISRM/SPE Symp., pp. 85–92, 1989.

Suarez–Rivera, F.R., Cook, N.G.W., Cooper, G.A., Zheng, Z.: "Indentation by Pore Collapse in Porous Rocks"–Rock Mechanics Contributions and Challenges, pp. 671–678, 1990.

Suarez–Rivera, F.R., Cook, P.J., Cook, N.G.W., Myer, L.R.: "The Role of Wetting Fluids During the Indentation of Porous Rocks"–Rock Mechanics as a Multidisiplinary Science, Proc. 32nd U.S. Symp., pp. 683–692, 1991.

(List continued on next page.)

*Primary Examiner*—Hezron Williams
*Assistant Examiner*—Jay L. Politzer
(74) *Attorney, Agent, or Firm*—Rosenthal & Osha L.L.P.

(57) ABSTRACT

A method for selecting a drilling parameter is disclosed. The method includes determining a loading displacement relationship for samples of earth formations. The loading displacement measurements are made by an indenter. The drilling parameter is selected from the loading displacement relationship. In one embodiment of the invention, the loading displacement relationship is determined from cuttings made during drilling of a wellbore. The loading displacement relationship determined during drilling is used to select at least one drilling parameter during drilling to improve drilling performance. Drilling parameters which can be selected include mill tooth and/or insert bit type; type of gauge protection to be used on the bit; type, size and orientation of jet nozzles on the bit; and blade structure, cutter type and density as well as the cutter impact resistance for fixed cutter bits. Other drilling parameters include weight on bit, drill bit rotation rate, and drilling fluid flow rate.

18 Claims, 5 Drawing Sheets

OTHER PUBLICATIONS

Zuasa, F. and Santarelli, F.J.: "A New Method to Determine Rock Strength from an Index Test on Fragments of Very Small Dimension". VIII ISRM International Congress on Rock Mechanics, Tokyo, Japan, pp. 114–117, 1995.

Ringstad, C., Loftus, E.B. Sonstebo, E.F., Fjaer, E., Zausa, F. and Giin–Fa Fuh: "Prediction of Rock Parameters from Micro–Indentation Measurements: The Effect of Sample Size". Paper SPE 47313 SPE/ISRM–EUROCK '98, pp. 487–492, Trondheim Jul. 8–10, 1998.

Santarelli, F.J., Detienne, J.L., Zundel, J.P.: "The Use of a Simple Index Test in Petroleum Rock Mechanics", Rock Mechanics as a Multidisiplinary Science, Proc. 32nd U.S. Symp., pp. 647–655, 1991.

Santarelli, F.J., Marsala, A.F., Brignoli. M., Rossi E. and Bona N.: "Formation Evaluation from Logging on Cuttings". Paper SPE 36851, Proc. Eur. Petrol. Conf. (Milano), pp. 319–329, 1996.

Zausa, F., Civolani, L., Brignoli, M. and Santarelli, F.J.: "Real Time Wellbore Stability Analysis at the Rig–Site". Paper SPE/IADC 37670–SPE/IADC Drilling Conference, Amsterdam, The Netherlands, pp. 837–846, Mar. 4–6, 1997.

Mason, K.L.: "Three–Cone Bit Selection With Sonic Logs", SPE Drilling Engineering, vol. 2, No. 1; pp. 1, 135–142, 1987.

Carter, J.A. and Akins, M.E.: "Dome PDC Technology Enhances Slim–Hole Drilling and Underreaming in the Permian Basin". Paper SPE 24606, 67th Annual Technical Conference & Exhibition of the Society of Petroleum Engineers; Washington, D.C.; pp. 645–665, 1992.

Moran, D.P.: "Dome Shaped PDC Cutters Drill Harder Rock Effectively". Oil and Gas Journal, vol. 90, No. 50; pp. 46–51, 1992.

Carminati, S., Del Gaudio, L., Zausa, F., and Brignoli, M.: "Hoe do Anions in Water Based Muds Affect Shale Stability". Paper SPE 50712. SPE International Symposium on Oilfield Chemistry., Houston, Texas, pp. 119–131, Feb. 16–19, 1999.

Jeff S. Arbogast and Mark H. Franklin, "Artificial Neural Networks and High–Speed Resistivity Modeling . . . Poweful New Exploration and development Tools"; Hart's Petroleum Engineer International Magazine (in two parts), May and Jun., 1999.

D. Dashevskly et al. "Application of Neural Networks for Predictive Control in Drilling Dynamics"; Society of Petroleum Engineers 56442, 1999 SPE Annual Technology Conference and Exhibition, Houston, Texas; Oct. 3–6, 1999.

Printed internet site entitled "DBOS SERVICES Drill Bit Optimization System", Printed Mar. 1, 2001, 2 pages www-.geodiamond.com/dbos/dboxhome.htm.

Printed internet site entitled "SINTEF Petroleum Research, Indirect Determination of USC", Printed Jan. 30, 2001, 2 pages, www.iku.sinteff.no/Formtys/activities/Cuttings/page4.htm.

METHOD FOR OPTIMIZING DRILL BIT DESIGN PARAMETERS

CROSS REFERENCE TO RELATED APPLICATIONS

This application claims to the benefit of U.S. Provisional Application No. 60/157,444, entitled "Method for Optimizing Drill Bit and Drilling Parameter Selection using Rock Strength Measurements made from Drill Cuttings", filed Oct. 4, 1999.

BACKGROUND OF THE INVENTION

1. Field of the Invention

The invention relates generally to the field of wellbore drilling. More specifically, the invention relates to methods for selecting the type of drill bit used, and the drilling parameters used to drill a wellbore so as to optimize the overall drilling performance.

2. Description of the Related Art

Methods known in the art for selecting the type of drilling bit are typically based on analysis of data related to the drilling performance achieved on previously drilled wells in the vicinity of the wellbore being drilled (called "offset wells"), and are based on monitoring and analysis of dull ("worn out") drill bits. Other methods known in the art for bit selection include methods for simulating ("modeling") the formation "drillability" and other drilling performance parameters. The drillability of earth formations is related to mechanical properties of the formations, in particular the compressive strength. Knowledge of the mechanical properties is useful to optimize the drilling of the formations. One well known method to determine compressive strength is based on acoustic ("sonic") well log interpretation combined with lithological analysis of formation data. Even though it is sufficiently reliable to calculate rock strength, the prior art method has two limitations: first, that the compressive strength is derived in this method from elastic theory, relating the rock acoustic responses to rock hardness, therefore the measurement is not a direct determination of strength; and second, that the acoustic log is recorded after the formation is completely drilled, and is therefore not useful for predictive analysis in the particular wellbore being drilled.

SUMMARY OF THE INVENTION

The invention is a method for selecting at least one drilling parameter for drilling a wellbore through earth formations. The method includes determining a loading displacement relationship of samples of earth formations from measurements of loading displacement made on the samples by an indenter. The at least one drilling parameter is selected from the loading displacement relationship thus determined.

In one embodiment of the invention, the loading displacement relationship is determined from drill cuttings made during the drilling of a wellbore. The relationship thus determined during drilling is used to select the at least one drilling parameter during drilling of the wellbore to improve drilling performance.

Drilling parameters which can be selected by the method of the invention include, but are not limited to, mill tooth and/or insert bit type when roller cone drill bits are used; whether and what type of gauge protection is to be used on the drill bit; type, size and orientation of jet nozzles to be included on the drill bit; and where fixed cutter bits are used, the blade structure, cutter type and density as well as the cutter impact resistance can be selected. Other drilling parameters which can be selected using the method of the invention include weight on bit, drill bit rotation rate, and drilling fluid flow rate.

In a particular embodiment of the invention, values of a slope of displacement with respect to applied force for the loading displacement measurements on each of the samples are characterized with respect to a measured compressive strength for each of the samples. The characterization is used in this embodiment to determine a compressive strength for samples of rock during drilling of the wellbore.

DETAILED DESCRIPTION

The invention uses a technique for determining the compressive strength of a sample of earth formation known as the "indentation technique". The indentation technique can be described as a quick, low cost test to determine rock mechanical properties from small rock fragments. Being an "index" test it allows production of an index value, directly related to rock properties, by means of a simple statistical analysis and simple rules of thumb. Research directed to establishing the theory and response of the indentation test is described in references numbered 1 through 6 in the Appendix.

Figures 1A, 1B:
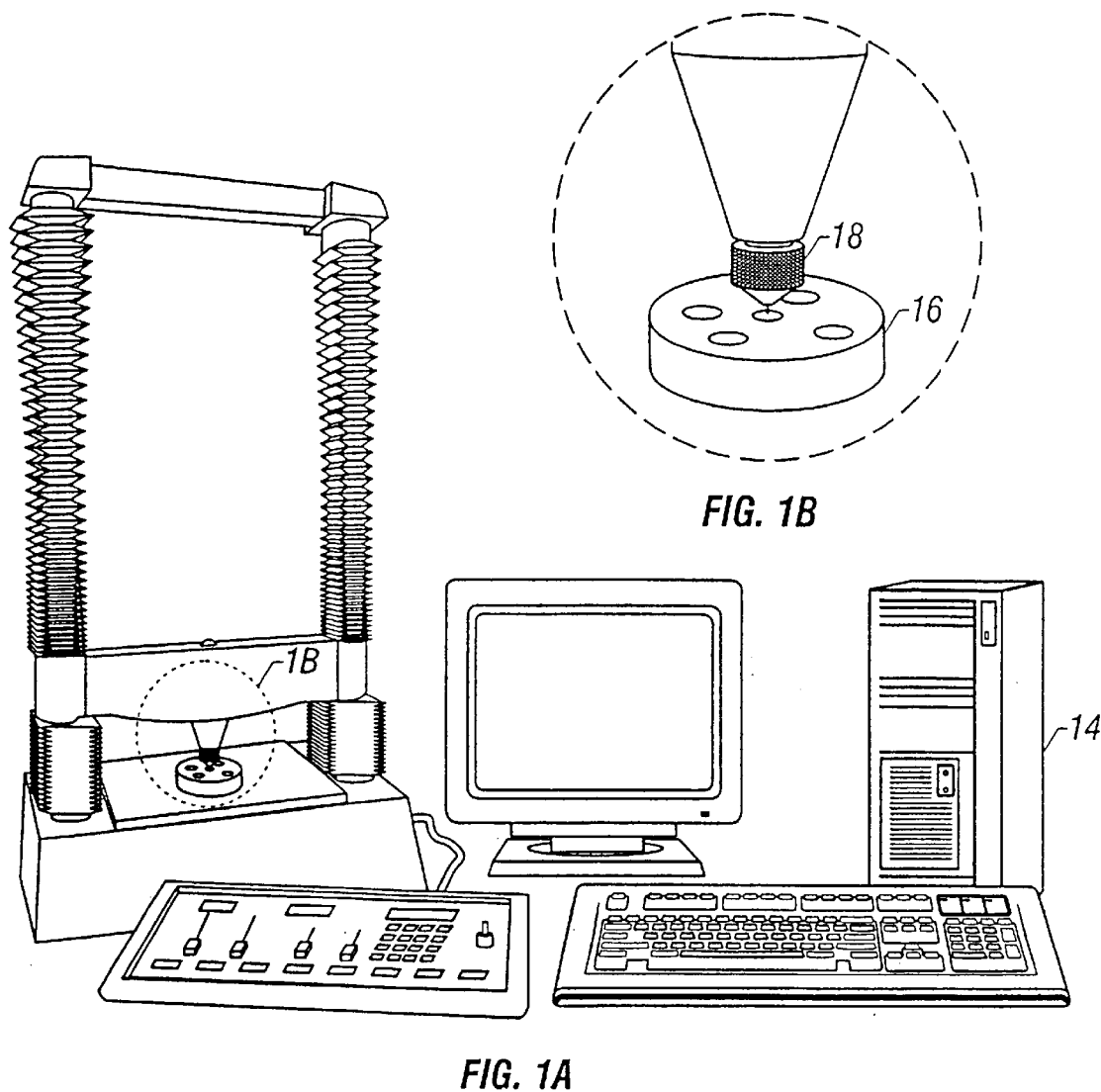
FIGS. 1A and 1B show one type of an indenter apparatus used to measure compressive strength of rock samples.

The indentation test can be generally described as a measure of the penetration of an indenter, shown generally at 10 in FIG. 1A into a small rock fragment, 16 in inset FIG. 1B, produced by the cutting action of a drill bit (see references 7 and 8 in the Appendix). These fragments are known as "cuttings". The indenter 10 has a stylus, 18 in FIG. 1B thereon with well defined geometrical features, shape and dimensions. The measure of penetration of the stylus 16 into the rock fragment 18 is made under precisely determined loading conditions,. The principle of the indenter test can be summarized as follows:

- a substantially constant load is applied to the cuttings (rock fragment 16) surface, which is shaped by proper flattening, in order to assure a load is applied in a normal direction, this being necessary to correctly interpret the testing results;
- the indenter 10 is forced at a constant loading rate up to the maximum penetration defined; and
- a loading-displacement curve is then recorded, such as on a computer (14 in FIG. 1A), and is analyzed to recover a penetration index value. The penetration index value is correlated with the mechanical rock behavior.

Figure 2A:
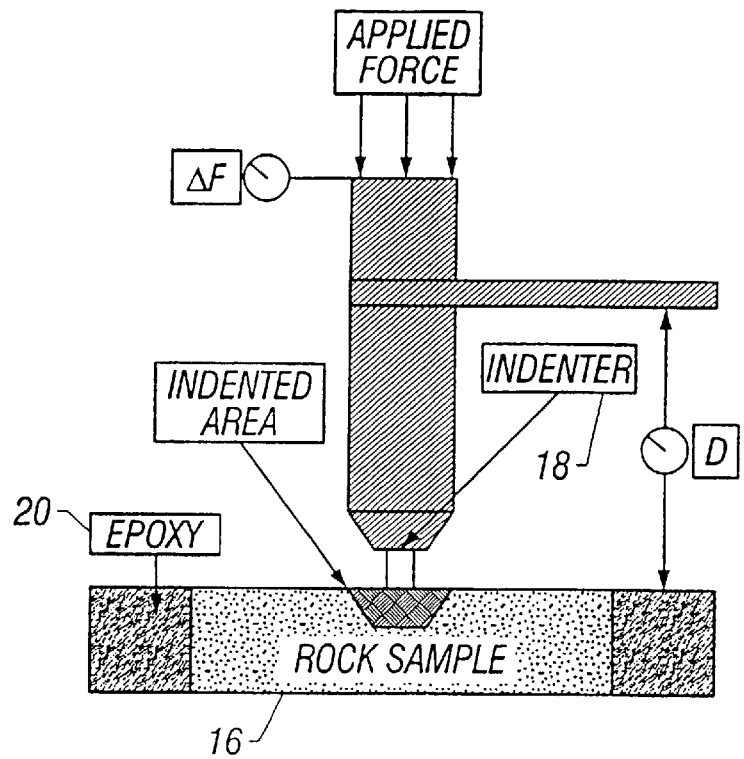
FIGS. 2A and 2B illustrate the principle of measurement of compressive strength from indenter measurements.
Figure 2B:
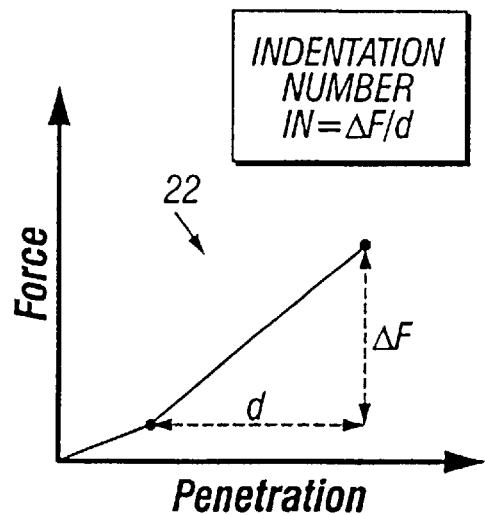

The principle of measurement using the indenter 10 is illustrated in FIG. 2A, wherein the rock sample is shown at 16, the indenter stylus at 18, and in FIG. 2B the correspondence between load applied and an example of the displacement, d, of the indenter stylus 18 with respect to normal force applied, F, is shown in the graph at 22. As shown in FIG. 2B, the indentation index number IN is defined as the slope of a linear portion of the graph of displacement d with respect to change in force ΔF.

Variables affecting the response of the indentation test are important to recognize in order to interpret the test results properly. A suitable way to prepare cutting samples and a standard test procedure have been defined to assure consistent results. One aspect of the indentation test, when performed on drill cuttings, is the sample preparation. In this embodiment of the invention, the cuttings are embedded in epoxy resin, as shown at 20 in FIG. 2A, in order to ultimately create a disk-shaped specimen 16. It should be understood that other means for assuring that the indenter applies normal force to the cuttings can be developed, and that the sample preparation method described here is not meant to limit the invention. After the resin 20 is cured, one face of the specimen 16 is trimmed and cut parallel to the opposite face to expose a sufficient number of cuttings to enable force measurement by the stylus 18 into the rock fragment. It should be noted that when dealing with highly porous rock, it is possible for the resin to invade the pore spaces of the rock, which may bias the measurement. To mitigate resin infiltration of such porous samples, a viscous resin having a short cure time can be used. A 1 millimeter cylindrical flat indenter stylus has been used in testing the invention, but the size and shape of the indenter stylus are not limitations on the invention.

Six to eight indentations are typically performed on each specimen by applying a constant penetration rate equal to about 0.01 millimeters per second, to a maximum penetration depth of about 0.3 mm. The corresponding loading-displacement curves are then measured during both a "loading" and "unloading" phase of the measurement. The measurements are typically stored on a computer (14 in FIG. 1A) for later processing and interpretation. As previously explained, an indentation index is defined herein as the slope of a substantially linear part of the loading displacement curve (as shown in graph 22 in FIG. 2B).

The above described indentation testing procedure has been evaluated to correlate the indentation index with a mechanical parameter (see references 9 and 10 in the Appendix). The results of the evaluation showed that generally six to eight cutting tests on each specimen should be performed so that the test results are representative of formation compressive strength, but a greater number of tests may be performed. The number of such tests on any individual specimen, therefore, should not be construed as a limitation on the invention. A direct correlation has been determined to exist between the indentation index and the uniaxial compressive strength ("UCS") as shown at curve 30 on the graph in is FIG. 3.

The samples can be analyzed after a wellbore is drilled, but in one aspect of the invention, the cuttings can be collected and analyzed during the drilling of a wellbore. During drilling of a wellbore, the cuttings can be collected directly at the "shale-shaker" on the drilling rig, at suitable drilled depth intervals, such as every ten meters (30 feet), when a lithological variation is detected in the cuttings, or by other detection techniques. The collected cuttings can then cleaned to remove drilling fluid ("mud") therefrom and then can be sorted according to size ("sieved") to a size range of between 2 mm and 5 mm. to avoid contamination by "cavings" (rock fragments which have fallen down from the upper wall of the wellbore). The sieving size range specified herein is not intended to limit the invention. A sufficient number of cuttings can be gathered, embedded in epoxy, as shown generally at 20 in FIG. 2A, and prepared as previously explained to obtain a disk-shaped specimen for each depth interval to be analyzed. Cuttings in each specimen can then be tested, and a collection of loading displacement curves obtained for each specimen. Three possible values of the mechanical properties have been considered:

the indentation index value for each tested rock sample;

a mean value of the indentation indices for each rock sample, computed as an arithmetical average from the slope measured for each loading displacement curve; and the mean of all the loading-displacement curves from which is calculated a corresponding slope (indentation index), such as shown in FIG. 2B.

Figure 3:
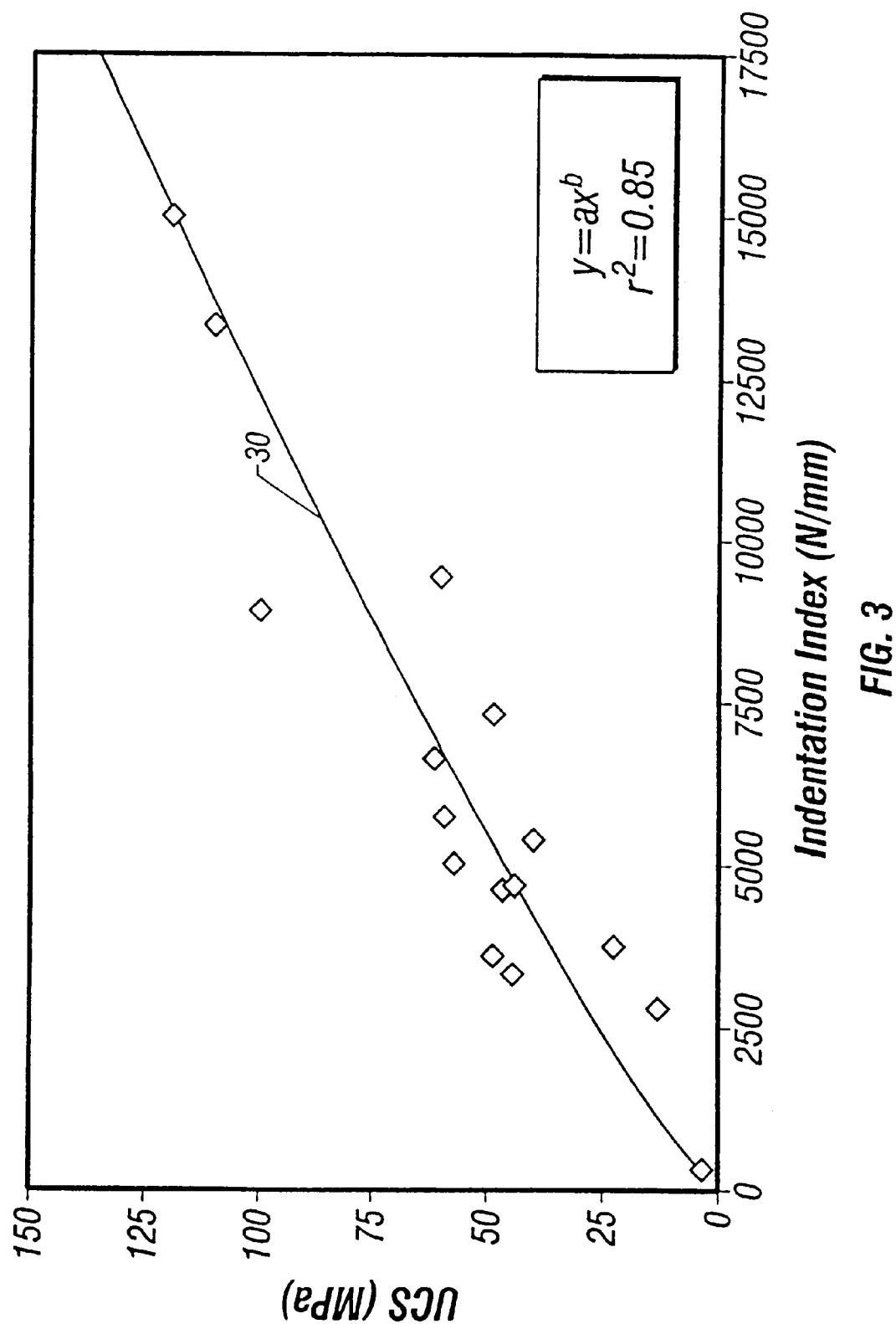
FIG. 3 shows an empirically determined correspondence between unconfined compressive strength and the indenter measurements.

The slope thus determined is then used, in conjunction with a relationship such as shown in FIG. 3, to determine an unconfined compressive strength of the formation whose cuttings are in each specimen. Every depth interval for which a specimen has been made can then be characterized according to mechanical properties, including compressive strength of the rock cuttings in the associated specimen.

After the compressive strength of the cuttings in each of the specimen is determined by the indentation testing as just described, a drill bit optimization analysis is then performed to determine the most likely optimum drill bit cutting structure and other bit design features, as well other drilling parameters such as hydraulic requirements, gauge protection, the axial force (weight) applied to the bit, and the bit rotation rate. The optimization can be performed for both roller cone and fixed cutter drill bits. Several different types of drill bit optimization systems are known in the art. For example, one such system is sold under the trade name DBOS™ by Smith International, Inc., Houston, Tex. Other drill bit optimization systems known in the art include: RSA™ service sold by Reed-Hycalog, Houston, Tex.; GEO-MECHANICS™ service sold by Dresser Industries, Inc. (now owned by Halliburton company); and ROCKY™ service sold by Baker Hughes Incorporated, Houston, Tex. It is to be clearly understood that the particular type of drill bit optimization program is not meant to limit the invention. The foregoing optimization programs are provided herein only as examples of programs that are useful with the method of this invention.

An important input parameter to the drilling bit optimization program or analysis is the compressive strength of the formations through which the wellbore is drilled. In the prior art, as previously explained, acoustic well logs, combined with other well logs, have been used to predict formation drillability (see references 12, 13, 14 and 15 in the Appendix) by estimating compressive strength. The use of indentation testing, as provided in this invention, to predict drillability can have several advantages when used in a drill bit optimization program or analysis:

indentation testing does not correlate a dynamic property with a mechanical one, but provides a direct measure of properties related to the mechanical features of the rock;

indentation testing allows a continuous monitoring of formation strength along the wellbore section being drilled;

indentation testing is a "while drilling" measurement performed directly at the rig site and allows the possibility to adjust the forecasted strength with the values measured during drilling.

A brief description of the parameters calculated, for example, by the DBOS™ drilling optimization service sold by Smith International, Inc. will be presented, analyzing therefor the main characteristics, and particularly those aspects related to formation compressive strength. It should be clearly understood that the method of this invention can be used with any other type of drilling optimization program or drilling optimization analysis which uses compressive strength as an input parameter.

It should also be clearly understood that any drilling optimization program which uses compressive strength as input for calculating or determining bit design parameters and/or drilling operating parameters can be readily modified to accept as an alternative input the slope of the loading displacement relationship determined for any particular earth formation sample. The contemplated modification includes a calculation of a value of compressive strength according to a relationship such as shown in FIG. 3 from measurements of loading displacement such as shown in FIG. 2B.

The first step of the typical drilling optimization program is formation analysis, through reconstruction of the lithologies within a given stratigraphic section. Formation analysis relies on:
- offset well log information, such as from gamma ray, acoustic velocity, bulk density, and neutron porosity;
- "mud log" analysis to provide formation descriptions of accessory minerals not determined from well log response, and to verify the well log determined lithology;
- rate of penetration ("ROP") data, weight on bit ("WOB") data and drill bit rotary speed ("RPM") for better post-drilling analysis of drill bit performance.

Figure 4A:
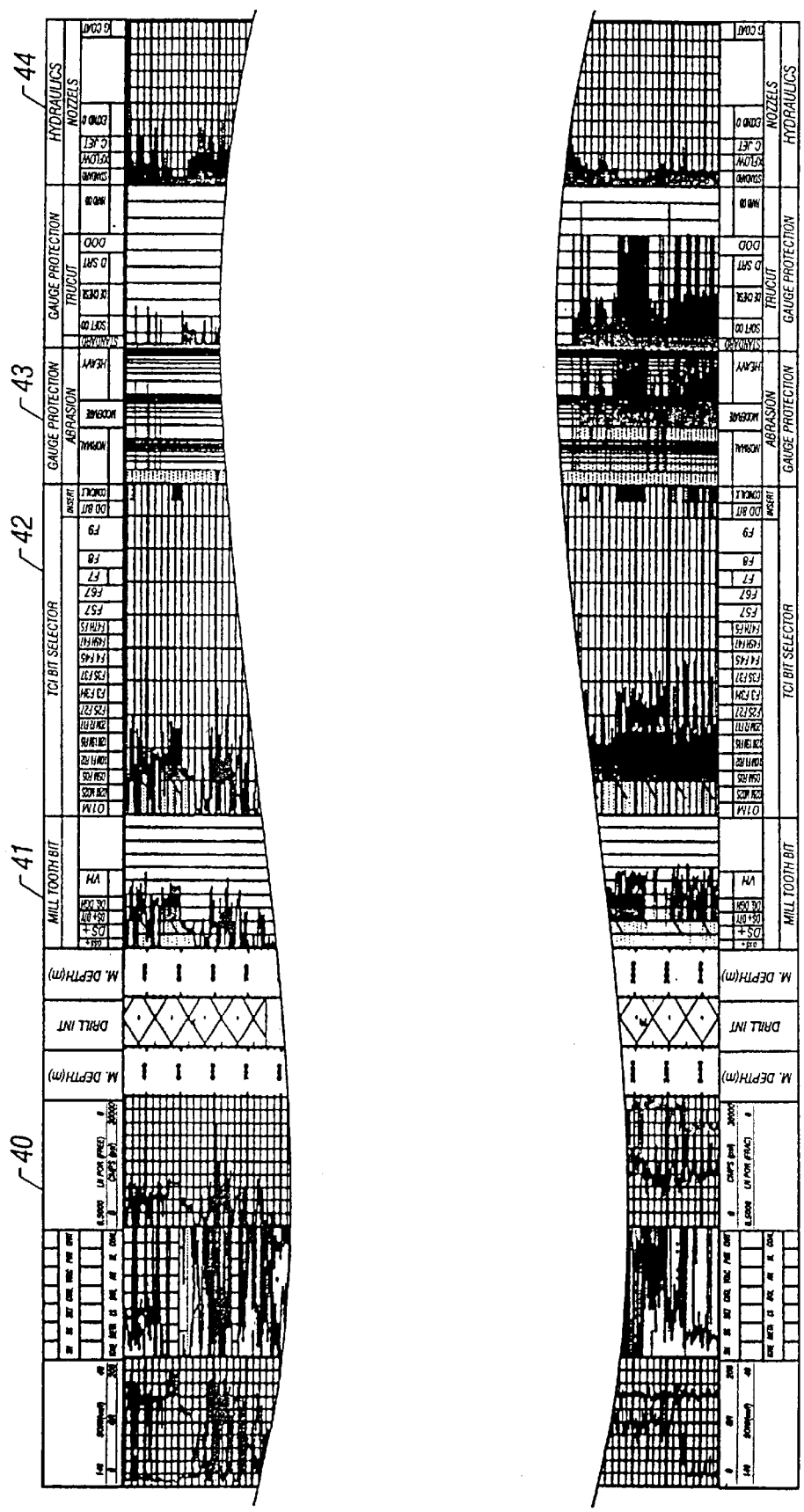
FIG. 4A shows an example Rock Bit Selector plot for roller cone bits using as input the compressive strength values determined from the method of the invention.
Figure 4B:
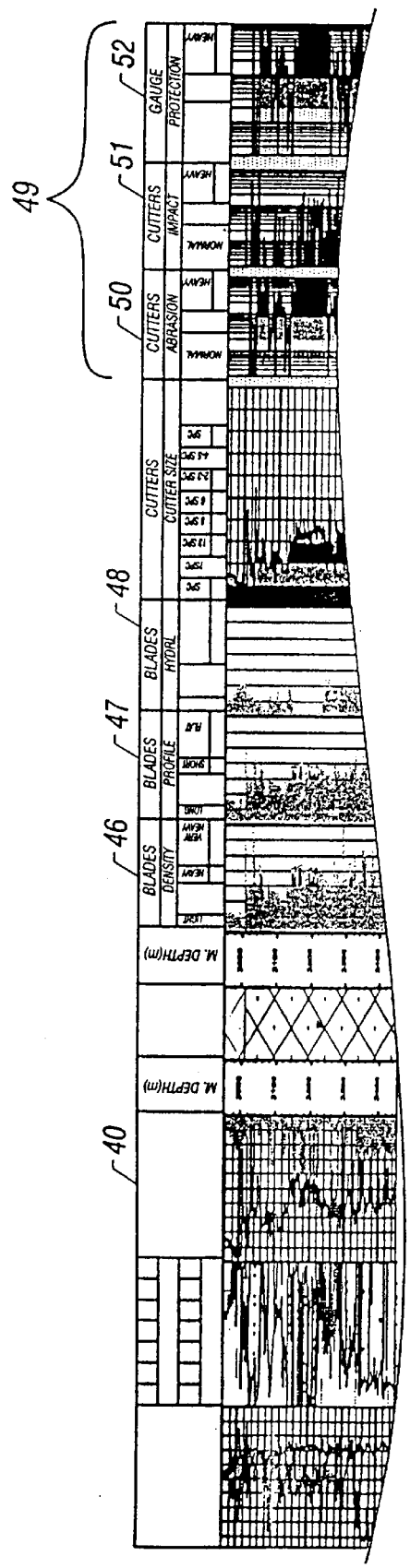
FIG. 4B shows an example of a Rock Bit Selector plot for fixed cutter bits.
Figure 4B:
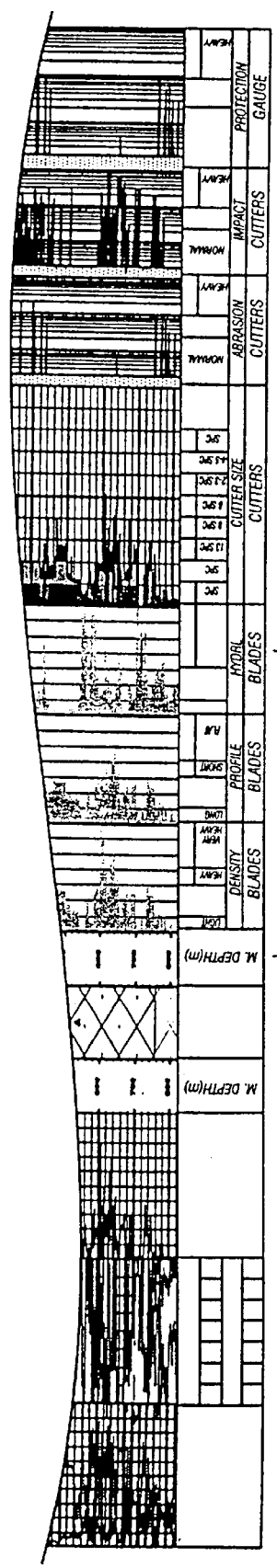

The next part of the process is bit performance analysis. Bit record information, directional surveys, and/or real time rate of penetration ("ROP") and drilling parameters (including rotary bit speed and axial force on bit, for example) from "mud log" data are incorporated into the typical bit performance analysis. FIGS. 4A and 4B show such an analysis in a "well log" plot format.

Variables affecting drill bit performance within a formation having a particular drillability can be evaluated using techniques such as by bar graph distribution, or by focusing on a single bit run. Once data have been input to the program, a lithology column is generated and unconfined rock compressive strengths (UCS) are calculated. Offset wellbore data can be divided into sections or intervals, based on "geomechanical units" (often incorporating several geological units) or "lithologic units". Several parameters are evaluated statistically for each drillability interval:
- Lithology Normalized ("LN") Porosity is evaluated and is used later to more accurately determine bit hydraulic design and nozzle requirements. Gas zones are identified and rock strengths are then corrected;
- Unconfined rock compressive strengths are then statistically calculated and, combined with the dominant rock type, later applied to rock bit selection and cutter density and bit profile recommendations for fixed cutter bit applications. Further sand content (quartz-bearing formations) combined with rock strength contributes to the model's determinations of formation abrasiveness;
- Fractional volume of shale variations from interval to interval, together with acoustic velocity (or transit time) are used to determine optimal types of hydraulic nozzling, where porosity logs are unavailable.

The Rock Bit Selector ("RBS") output of the DBOS program compiles the results of the bit type and feature selection in a "well log" plot format as shown in FIG. 4A. The following can be presented on the RBS plot as shown in FIG. 4A:

source data 40 from any offset wells including gamma ray, acoustic travel time or velocity, any well log-determined lithologies, the calculated unconfined rock strength, log normalized porosity, drillability intervals, and true vertical depth;

a mill tooth bits output column 41 which indicates bit types based on combinations of dominant rock type and formation compressive strength, ranging from International Association of Drilling Contractors (IADC) standard bit code 11, to 21-type bits. Note that intervals having similar drillability become apparent when observing the bit type suggested in the output column.

tungsten carbide insert (TCI) bits column 42, ranging from IADC Code 41 to 83-type bits. These selections are made in parallel with the mill tooth bit selection.

insert type bits column with the various insert types depending on specific application. 'DD' bits are designed with diamond enhanced TCI inserts (of various shapes) deployed across the entire bit face and are suitable when quartz-bearing rocks dominate the overall lithology. Conical Inserts are preferred over standard chisel inserts where shale fractional volumes are low and where rock strengths indicate that at least an IADC Code 44-type cutting structure should be used.

gauge protection column 43, wherein an abrasion function is determined by a combination of sand (quartz) content and rock strength. If sand content exceeds a predetermined "normal" condition, the program will generate an indication of how extreme the abrasive wear characteristics the particular formation is likely to have. The DBOS program then calculates an indication of the need for enhanced gauge protection based on the abrasion indicator and/or bit dull gauge wear conditions from any offset well data. In this column three increasing levels of abrasiveness are defined:
1. Soft formation—Standard (no enhancement needed), soft 'OD' (diamond enhanced heel row applied to aggressive soft formation bits), D/E Chisel (diamond inclined gauge chisel).
2. Medium formation—'D' feature (diamond Semi Round Tops—(SRT)—in the gauge row position), 'DOD' (diamond SRT's in both gauge and heel row positions).
3. Hard Formation—'OD' feature (diamond SRT's again in the heel row position—for hard formation bits).

Hydraulics/Nozzling. The hydraulics column 44 indicates jet nozzle requirements to maintain proper bit cleaning, assuming adequate mud flow rates and hydraulic horsepower. Based on lithology normalized (LN) porosity and/or acoustic velocity and shale content analysis, indicators are presented for the following jet types:
1. Standard (no enhancement).
2. Crossflow (asymmetric flow patterns).
3. Center jetting.
4. Extended Nozzles A Fixed Cutter Bit Selector ("FCBS"), shown in FIG. 4B, similar to the Rock Bit Selector previously described, uses the formation characterization, rock strength and offset dull bit condition to assess the aspects of PDC/natural diamond bit design appropriate for the application. Again a well log plot form is generated, showing:
Source Data from the offset well as previously described, and as shown at 40.
Blade/Body Design to evaluate the "architectural" aspects of the bit head, as shown at 45.
Density: either or both cutter density and blade count as a quantitative function of rock strength. Density ranges from light (3–4 blades) to heavy (12 or more blades), as shown at 46.

Bit profile, evaluates both PDC and Natural Diamond bits. A statistical histogram, for a certain depth interval, indicates the optimum survivable profile, as shown at 47.

Hydraulic Design or blade "architecture", as shown at 48, refers to the height of the blade above the body or relative openness of the bit face. Hole cleaning is determined considering shale porosity derived from the log normal porosity curve. If no porosity data is available then shale volume and/or acoustic velocity analysis can be used.

Cutter size determinations, shown at 49 based on a combination of dominant rock type and acoustic velocity. Optimal PDC cutter sizes can be evaluated statistically across the interval of interest, ranging from 19 mm (¾") for softer formations to natural diamond stone sizes (5–6 stones per carat) to impregnated bits for harder formations. Statistical distributions that overlap cutter sizes would justify multiple cutter bit designs.

Abrasion, as introduced above, and as shown at 50 in FIG. 4B, based on combinations of sand content and rock strength. The DBOS program determines a sand content with respect to the rock strength at each foot as a "normal" abrasive condition. If the actual sand content exceeds this condition, the program calculates how excessive or abrasive the formation is likely to be given such sand content. The data are presented in a well log plot format and, indicating increasing levels of abrasivity, recommend for premium abrasive resistant cutters where appropriate.

Impact resistance, shown at 51, measuring the rate of change in rock strength for two consecutive depth levels. In a manner similar to the calculation for abrasivity, the program determines how much the impact excess is likely to be generated by the particular formation. The data are presented in well log plot format just as for the abrasion plot. This output indicates where premium impact resistant cutters are indicated and/or where bit vibration reducing systems are advisable for the intended application.

Gauge Protection, shown at 52, as a continuous function of formation abrasivity and/or offset bit gauge wear condition. The data, presented in well log plot format, indicate heavy gauge protection requirements and suitable gauge pad technology where appropriate.

A methodology has been developed to improve drill bit design parameter selection and drilling operating parameter selection using measurements which directly correspond to formation compressive strength made on drill cuttings as input data to a drill bit optimization system. Some possible advantages can be pointed out considering a direct measure of formation compressive strength instead of an estimated one:

1. The testing conditions are extremely fast and simple but sufficiently reliable to correctly determine rock strength.
2. Portable equipment exists to run this test, allowing the possibility of applying the whole methodology as a real time tool to adjust the predicted drilling plan.
3. Continuous information can be recovered along the whole wellbore.
4. It is an inexpensive methodology.
5. The possibility of directly measuring rock compressive strength at the drilling rig-site can allow the selection of more aggressive cutting structures compared to those generally used in earth formations, thereby improving drilling performance.

While the foregoing description of the invention is limited to only one example, those skilled in the art will appreciate that other embodiments of the invention can be readily devised which do not depart from the spirit of the invention as disclosed herein. Accordingly, the invention shall be limited in scope only by the attached claims.

What is claimed is:

1. A method for selecting parameters for drilling a wellbore through earth formations, comprising:

determining a loading displacement relationship from measurements made by an indenter on samples of selected earth formations obtained during drilling of the wellbore;

characterizing said loading displacement relationship with respect to a compressive strength of said selected earth formations, the characterizing comprising measuring said loading displacement through a preselected displacement range on samples of a plurality of selected earth formations, determining a substantially linear portion of said relationship for each of said samples from said plurality of formations and correlating a slope of said substantially linear portion for each of said samples from said plurality of formations to a measured compressive strength of each of said samples from said plurality of formations; and selecting at least one drill bit design parameter during the drilling of the wellbore based on said loading displacement relationship.

2. The method as defined in claim 1 further comprising determining a compressive strength of at least one additional formation sample, comprising:

performing a loading displacement test on said at least one additional sample;

determining a slope of a linear portion of the loading displacement relationship performed on the at least one additional sample; and determining the compressive strength of the at least one additional sample from the correlation of the slopes of the each of said samples from said plurality of formations to the measured compressive strength of each of said samples from the plurality of formations.

3. The method as defined in claim 1 wherein said at least one additional sample is taken from a wellbore during drilling thereof, and said at least one drill bit design parameter is adjusted in response to a slope of a linear portion of said loading displacement relationship determined for said at least one additional sample taken during said drilling of said wellbore.

4. The method as defined in claim 1 wherein said at least one drill bit design parameter comprises mill tooth type on a roller cone drill bit.

5. The method as defined in claim 1 wherein said at least one drill bit design parameter comprises insert type on a roller cone drill bit.

6. The method as defined in claim 1 wherein said at least one drill bit design parameter comprises gauge protection type.

7. The method as defined in claim 1 wherein said at least one drill bit design parameter comprises jet nozzle type and orientation.

8. The method as defined in claim 1 wherein said at least one drill bit design parameter comprises at least one of bit profile, cutter density, cutter type and cutter impact resistance on a fixed cutter drill bit.

9. The method as defined in claim 1 further comprising selecting at least one of weight on bit, bit rotation rate and drilling fluid flow rate based on said loading displacement relationship.

10. The method as defined in claim 1 wherein said samples are disposed in a resin, said resin is cured, and a test specimen is generated therefrom by grinding a substantially parallel flat surfaces on said cured resin.

11. A method for selecting drilling parameters, comprising:
   measuring a loading displacement relationship through a preselected displacement range on at least one sample of at least one earth formation collected during drilling of a wellbore;
   determining a substantially linear portion of said loading displacement relationship for said at least one sample;
   correlating a slope of said substantially linear portion of said at least one sample to a relationship of a compressive strength to a linear portion of a loading displacement relationship of other formation samples to determine a compressive strength of said at least one sample; and
   selecting at least one drill bit design parameter during the drilling of the wellbore in response to said determined compressive strength.

12. The method as defined in claim 11 wherein said at least one drill bit design parameter comprises mill tooth type on a roller cone drill bit.

13. The method as defined in claim 11 wherein said at least one drill bit design parameter comprises insert type on a roller cone drill bit.

14. The method as defined in claim 11 wherein said at least one drill bit design parameter comprises gauge protection type.

15. The method as defined in claim 11 wherein said at least one drill bit design parameter comprises jet nozzle type and orientation.

16. The method as defined in claim 11 wherein said at least one drill bit design parameter comprises at least one of bit profile, cutter density, cutter type and cutter impact resistance on a fixed cutter drill bit.

17. The method as defined in claim 11 further comprising selecting at least one of weight on bit, bit rotation rate and drilling fluid flow rate based on said loading displacement relationship.

18. The method as defined in claim 11 wherein said samples are disposed in a resin, said resin is cured, and a test specimen is generated therefrom by grinding a substantially parallel flat surfaces on said cured resin.

* * * * *